US009353028B2

(12) United States Patent
Merkel et al.

(10) Patent No.: US 9,353,028 B2
(45) Date of Patent: May 31, 2016

(54) REACTOR FOR LIQUID PHASE FLUORINATION REACTIONS

(71) Applicant: HONEYWELL INTERNATIONAL INC., Morristown, NJ (US)

(72) Inventors: Daniel C. Merkel, West Seneca, NY (US); Barry Asher Mahler, Glen Mills, PA (US); Hsueh Sung Tung, Getzville, NY (US); Mario Joseph Nappa, Newark, DE (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 14/618,500

(22) Filed: Feb. 10, 2015

(65) Prior Publication Data

US 2015/0225316 A1 Aug. 13, 2015

Related U.S. Application Data

(60) Provisional application No. 61/937,822, filed on Feb. 10, 2014.

(51) Int. Cl.
| *C07C 17/087* | (2006.01) |
| *C07C 17/20* | (2006.01) |
| *B01J 19/18* | (2006.01) |
| *C07C 17/25* | (2006.01) |

(52) U.S. Cl.
CPC ............... *C07C 17/087* (2013.01); *B01J 19/18* (2013.01); *C07C 17/25* (2013.01); *B01J 19/1868* (2013.01); *C07C 17/20* (2013.01); *C07C 17/206* (2013.01)

(58) Field of Classification Search
CPC ...... C07C 17/20; C07C 17/206; C07C 17/087
See application file for complete search history.

(56) References Cited

U.S. PATENT DOCUMENTS 5,773,651 A * 6/1998 Pfirmann ............ B01F 7/00016
562/456
8,058,486 B2 11/2011 Merkel et al.
(Continued)

FOREIGN PATENT DOCUMENTS

WO WO 9915268 A1 * 4/1999 ............... B01J 19/02
WO 2012/170239 A1 12/2012

OTHER PUBLICATIONS

International Search Report and Written Opinion issued in PCT/US2015/014759 mailed on May 29, 2015.

*Primary Examiner* — Fereydoun G Sajjadi
*Assistant Examiner* — Medhanit Bahta
(74) *Attorney, Agent, or Firm* — Scully Scott Murphy and Presser

(57) ABSTRACT

The present invention relates to a hydrofluorinating process which comprises reacting a fluoroolefin with hydrogen fluoride in the liquid phase in the presence of a hydrofluorination catalyst in the reaction zone of a reactor, said reactor comprised of a reactor body having a length to diameter ratio of about 2:1 or greater; a stirred reaction zone containing said hydrofluorination catalyst, which may be prepared in situ, at least one inlet for supplying said hydrogen fluoride and fluoroolefin to the reaction zone and at least one outlet for recovering said fluoroalkane, said stirrer disposed in the reaction zone and comprising a plurality of blades fixedly attached to shaft drivable by a motor, said blades extending from about the bottom of the reaction zone to about the top of the reaction zone and said shaft extending on a longitudinal axis from the bottom of the reactor to the top of the reactor, said stirrer being rotated at a speed sufficient to promote a swirling of the liquid to effect the occurrence of hydrofluorination reaction and minimize overfluorination. The present invention also relates to said hydrofluorination reactor.

23 Claims, 2 Drawing Sheets

(56) References Cited

U.S. PATENT DOCUMENTS

| | | |
|---|---|---|
| 8,581,012 B2 | 11/2013 | Tirtowidjojo et al. |
| 2012/0149951 A1 | 6/2012 | Mukhopadhyay et al. |
| 2012/0184785 A1 | 7/2012 | Cottrell et al. |
| 2014/0275648 A1* | 9/2014 | Chiu .................. C07C 17/25 570/156 |

* cited by examiner

REACTOR FOR LIQUID PHASE FLUORINATION REACTIONS

RELATED APPLICATION

The present application claims priority of U.S. Ser. No. 61/937,822, filed on Feb. 10, 2014, the contents of which are incorporated by reference.

FIELD OF THE INVENTION

Reactor designs useful for a process for liquid hydrofluorination reactions, especially hydrofluorination of fluorinated alkenes, for example, hydrofluorination of 2-chloro-3,3,3-trifluoropropene (HCFO-1233xf) to produce 2-chloro-1,1,1,2-tetrafluoro-propane (HFC-244bb), are described. These processes employ liquid phase fluorination reactions and the reactors are designed with this in mind.

BACKGROUND OF THE INVENTION

This invention especially relates to improvements in the production of 2,3,3,3-tetrafluoro-2-propene, also known as 1234yf, and having the chemical formula, $CF_3$—$CF$=$CH_2$.

This chemical compound has zero ozone depletion potential and low global-warming potential such that it may be useful and desirable as a replacement for existing materials used in refrigeration, foam blowing and other applications where fluorocarbons such as 1,1,1,2-tetrafluoroethane, also known as 134a, and known also by the chemical formula, $CH_2F$—$CF_3$, are currently utilized.

It is known in the art that 1234yf is produced from 1,1,2,3-tetrachloropropene (TCP or $CCl_2$=$CCl$—$CH_2Cl$) using a non-integrated three step route; (see for example U.S. Pat. No. 8,084,653, the disclosure of which is hereby incorporated herein by reference):

Step (1); TCP+3HF→1233xf+3HCl (where 1233xf is $CH_2$=$CCl$—$CF_3$)

Step (2); 1233xf+HF→244bb (where 244bb is $CF_3$—$CFCl$—$CH_3$)

Step (3); 244bb→1234yf+HCl

Hydrofluorination reactions, like that of Step (2) above, may be conducted in the liquid phase. In a commercial process, the objective is to conduct the conversion of 1233xf to 244bb with a conversion of greater than about 90% and with a selectivity of greater than about 90%. Since this is a heterogeneous reaction containing immiscible liquids and/or some solid catalyst material, in order to maximize the conversion of 1233xf to 244bb, it is important that the reactants and catalyst be uniformly mixed. One of the problems encountered and to overcome is channeling which creates potential eddy currents in addition to substantially dead spaces, all of which may lead to nonhomogeneous material treatment, thereby reducing the conversion of 1233xf and selectivity to 244bb.

The present inventors have developed an apparatus for use in liquid hydrofluorination reaction which tends to minimize the channeling effect and promote the conversion of a fluoroolefin to a fluorocarbon, for example, the formation of 244bb from 1233xf.

However, the conversion of the fluoroolefin is just one aspect of the problem. At the same time, the objective is to maximize the selectivity to 244bb by minimizing side reactions from the hydrofluorination reaction, such as overfluorination. For example, if the fluorocarbon produced has a suitable leaving group thereon, such as a chlorine atom, the fluorocarbon may undergo a subsequent substitution reaction with HF in which the fluorine atom substitutes for the leaving group. For example, in the hydrofluorination of 1233xf to form 244bb, the reaction of 244bb with a second molecule of HF to form 245cb, as indicated below, is a side reaction: 244bb+HF→HCl+245cb (where 245cb is $CF_3CF_2CH_3$). Further, the reaction of 1233xf with 2 moles of HF less to the formation of 245cb: 1233xf+24F→HCl+245cb Unless the reaction conditions can be adequately controlled, the formation of the second product from the reaction with hydrogen fluoride may not only decrease the yield of the 244bb fluorocarbon, but also decrease the selectivity to the 244bb fluorocarbon, i.e., it may instead increasingly promote the formation of the side reaction product. The present inventors have found a method which promotes only the hydrofluorination reaction to occur and minimizes the formation of the side products.

In addition to the channeling and the side reaction issues, another problem encountered in the liquid hydrofluorination process is the use of corrosive material. The hydrofluorination reaction uses and generates corrosive compounds, such as, for example, hydrogen fluoride and chlorine gas, the latter of which can be used to regenerate the hydrofluorination catalysts. Both tend to corrode the reactor in which the reaction is conducted, even reactors comprised of corrosion-resistant materials such as Inconel 600, NAR25-50MII, Hastelloy C, Hastelloy G-30, duplex stainless steel, and Hastelloy C-22. Corrosion of the reactor compromises the structural integrity of the reactor and reduces its useful life. Therefore, a need to minimize reactor corrosion exists.

Generally, reactors having a molded liner, such as a rotary-baked or sprayed-on liner, are not suitable for large-scale commercial production reactions. Reactors having such liners must be baked in large kilns or ovens, which are expensive and frequently unavailable. Indeed, fitting a large reactor, for example, greater than about 1,000 gallons, with a baked liner is impractical.

A molded liner not only imposes practical limitations on the size of the reactor, but also introduces additional structural limitations. It has been found that molded liners often tend to be permeable and, under high pressures and over time, reactants tend to penetrate the liner and develop pressure between the liner and the reactor wall. This pressure causes the liner to blister, and eventually the liner comes loose. The problem of liner penetration is exacerbated by the absence of weep holes in a molded-liner reactor. Ordinarily, weep holes allow reactants that penetrate the liner to escape from the reactor. A molded liner, however, generally cannot be used in a reactor with weep holes. When applying a molded liner, a fluid fluoropolymer is applied to the reactor wall, and, thus, holes in the reactor wall will result in holes in the molded liner. Holes in the liner obviously compromise the reactor's ability to be pressurized. Therefore, while a rotary-baked, fluorine-resin liner may minimize reactor corrosion, its structural limitations nevertheless limit the reactor's size and/or useful life.

Therefore, a need exists for a commercially viable method of producing a wide range of HFCs while minimizing reactor corrosion. The present invention fulfills this need among others.

SUMMARY

The present invention relates to a hydrofluorinating process which comprises reacting a fluoroolefin with hydrogen fluoride in the liquid phase in the presence of an hydrofluorination catalyst in the reaction zone of a reactor to produce a fluoroalkane, said reactor comprised of a reactor body having a length to diameter ratio of about 2:1 or greater; a stirred reaction zone containing said hydrofluorination catalyst; at least one inlet for supplying hydrogen fluoride and fluoroolefin to the reaction zone and at least one outlet for recovering said fluoroalkane, a stirrer disposed in the reaction zone and comprising a plurality of blades fixedly attached to a shaft drivable by a motor, said blades extending from about the bottom of the reaction zone to about the top of the reaction zone and said shaft extending on a longitudinal axis from the bottom of the reactor to the top of the reactor, said stirrer being rotated at a speed sufficient to promote a swirling of the liquid so to minimize channeling and so permit said stirring of the catalyst and fluoroolefin with the hydrogen fluoride to effect the occurrence of a hydrofluorination reaction and be maintained with a conversion of about 90% or greater and selectivity of about 90% or greater per catalytic run.

In another embodiment, the reactor additionally comprises a controller in communication with the stirrer wherein the controller is configured to control the rotation of the shaft and the plurality of blades.

Another embodiment of the present invention is directed to a reactor for the hydrofluorination reaction of a fluoroolefin to a fluoroalkane in the presence of a hydrofluorination catalyst comprising a reactor body having a length to diameter ratio of about 2:1 or greater; a stirred reaction zone containing the hydrofluorination catalyst, anhydrous hydrofluoric acid and fluoroolefin, at least one inlet for supplying said hydrogen fluoride and fluoroolefin to the reaction zone and at least one outlet for recovering said fluoroalkane, said stirrer disposed in the reaction zone and comprising a plurality of blades fixedly attached to a shaft drivable by a motor, said blades extending from about the bottom of the reaction zone to about the top of the reaction zone and said shaft extending on a longitudinal axis from the bottom of the reactor to the top of the reactor, said stirrer being rotated at a speed sufficient to promote a swirling of the liquid and to minimize channeling and so to permit said stirring of the catalyst and fluoroolefin with the hydrogen fluoride to effect the occurrence of hydrofluorination reaction and be maintained with greater than about 90% conversion and greater than about 90% selectivity per catalytic run.

In another embodiment, due to the corrosive nature of the reaction mixture, the reactor is lined with a fluoropolymer such as PFA (perfluoroalkoxy polymer) or PTFE (polytetrafluoroethylene polymer).

One embodiment of this invention is thus directed to a reactor design that may be used for the Step (2) reaction, namely the hydrofluorination of 2-chloro-3,3,3-tri-fluoropropene (1233xf) to 2-chloro-1,1,1,2-tetrafluoropropane (244bb) using a liquid phase reactor and fluorinated $SbCl_5$ as the liquid phase fluorination catalyst. This reactor design is referred to as a slowly stirred 'bubble column' liquid phase fluorination reactor.

One embodiment of a reactor designed for the Step (2) reaction comprises a fluoropolymer lining, preferably in a loose liner form, for ease of replacement. The reactor further comprises a relatively large length to diameter (L/D) ratio compared to commercial laboratory reactor designs and a unique stirrer to prevent channeling within the reaction mixture without compromising the integrity of the fluoropolymer liner.

In addition to the use of a large L/D ratio, the present invention uses a unique stirrer to prevent channeling of the reactants through the reactor. Thus, instead of a typical commercial mechanical agitator, the reactor design of this invention includes a multi-bladed stirrer with a plurality of offset stirrer blades that will rotate at less than about 200 rpm, for the purpose of eliminating channeling. The wetted stirrer parts can be made of, or lined with fluoropolymer corrosion resistant materials. The length of the blades should be such that they are within a relatively short distance from the inside wall of the reaction vessel to prevent channeling close to the walls.

DETAILED DESCRIPTION OF EMBODIMENTS OF THE INVENTION

Figure 1:
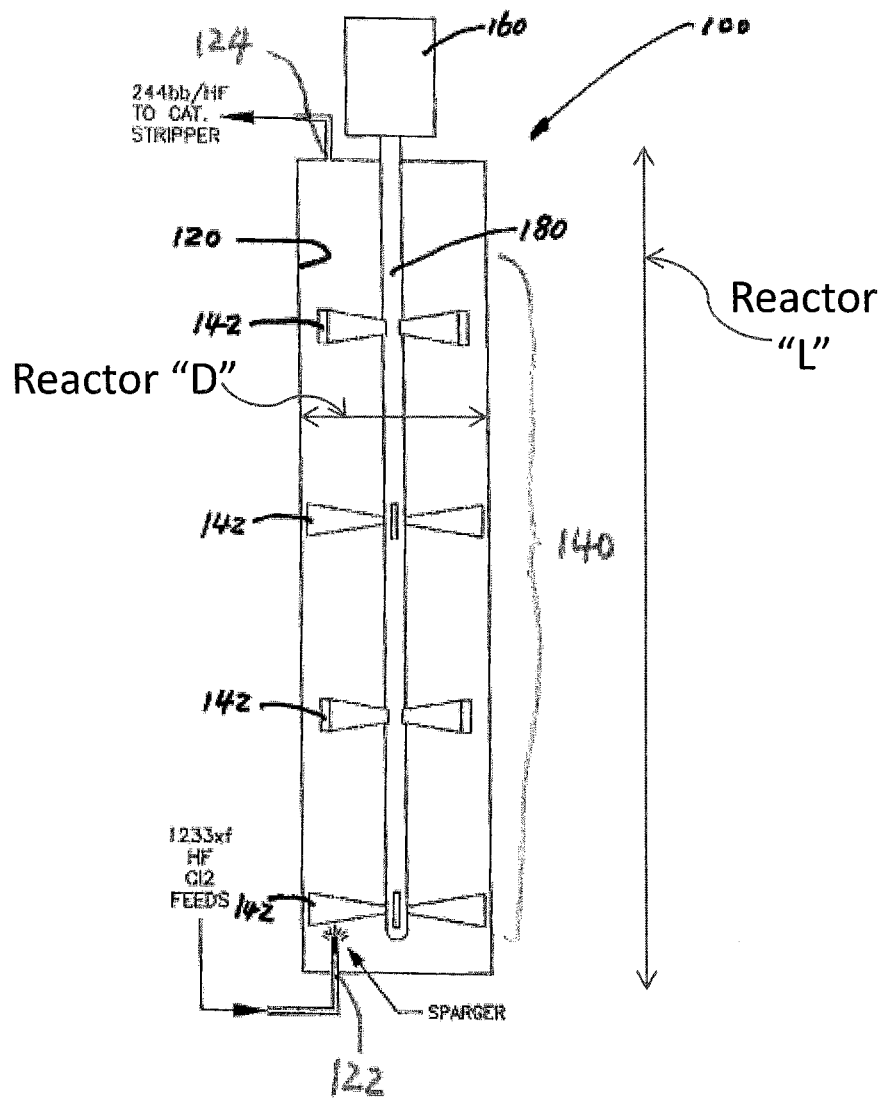
FIG. 1 is an illustrative sectional view of an embodiment of the slowly stirred bubble column reactor according to an aspect of the present invention, in which the L/D ratio is 6:1.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B is true (or present).

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

The term "fluoroolefin", as used herein, denotes a molecule containing hydrogen, carbon, fluorine, and at least one carbon-carbon double bond and optionally chlorine.

The term "fluoroalkane", as used herein, refers to an alkane having two or more carbon atoms containing hydrogen, fluorine, and optionally chlorine, whereby a fluorine atom and a hydrogen atom are substituted on two adjacent carbon atoms. As used herein, the fluoroalkane is the product from the hydrofluorination of the fluoroolefin.

The HF used herein is an anhydrous liquid hydrogen fluoride which is commercially available. It is sold by, for example, Solvay S.A, E. I. du Pont de Nemours and Company and Honeywell International, Inc.

The term "side product", as used herein refers to the products that are formed in the hydrofluorination reaction from the reaction of the desired fluoroalkane thus formed reacting with a second molecule of hydrogen fluoride. Thus, for example, the overfluorination product is a side product.

As used herein, the term "conversion" with respect to a reactant, which typically is a limiting agent, refers to the number of moles reacted in the reaction process divided by the number of moles of that reactant initially present in the process multiplied by 100.

As used herein, the term "selectivity" with respect to an organic reaction product refers to the ratio of the moles of that reaction product to the total of the moles of the organic reaction products multiplied by 100.

An aspect of the present invention is the process for the hydrofluorination of a fluoroolefin, while maximizing the formation of the desired fluorocarbon and minimizing the formation of side products. The reaction mixture for this process comprises HF, fluoroolefin and the hydrofluorination catalyst. In this reaction conducted in the liquid phase, the fluoroolefin is reacted with hydrogen fluoride in the presence of a hydrofluorination catalyst to produce a compound in which the hydrogen atom and the fluorine atom are added across the double bond to produce a fluoroalkane. An example is Step (2) in the formation of 1234yf from TCP; the hydrofluorination of 2-chloro-3,3,3-trifluoro-propene (1233xf) to 2-chloro-1,1,1,2-tetrafluoropropane (244bb) in a liquid phase using a liquid phase reactor and a liquid phase fluorination catalyst is as follows:

There is no hydrogen chloride present in this hydrofluorination reaction, which is not typical in many fluorination reactions. In many fluorination reactions for making refrigerants, HCl gas is produced, and the formation of the gas in situ provides the necessary agitation of the liquid so as to prevent the channeling effect described herein. This lack of HCl by-product formation is unique when compared to other well-known liquid phase fluorination reactions that produce CFCs (e.g., $CF_2Cl_2$), HCFCs (e.g., HCFC-22 or HCFC-142b), and HFCs (e.g., HFC-143a or HFC-245fa).

This reaction is conducted at effective temperatures for the hydrofluorination of the fluoroolefin to form the fluoroalkane to occur. For example, in an embodiment, the temperature for the hydrofluorination reaction ranges from about 70° C. to about 130° C., and in another embodiment, from about 83° C. to about 120° C., and in another embodiment, from about 85° C. to about 95° C.

The hydrofluorination catalysts used in this reaction are liquid fluorination catalysts normally used in hydrofluorination reactions. They are Lewis acids. The catalysts which may be used include $AlF_3$, $BF_3$, $FeCl_{3-a}F_a$ (where a=0 to 3), $FeX'_3$ supported on carbon, (where each X' is independently a halide, such as F or Cl or Br, and in an embodiment, all X's are the same), $SbCl_{3-b}F_b$ (b=0 to 3) $AsF_3$, $MCl_{5-c}F_c$ (where c=0 to 5 and M=Sb, Nb, Ta, or Mo), and $M'Cl_{4-d}F_d$ (where d=0 to 4, and M'=Sn, Ti, Zr, or Hf). In another embodiment, catalysts for the liquid phase process are $MCl_{5-e}F_e$ (where e=0 to 5 and M=Sb, Nb, or Ta).

In an embodiment, the hydrofluorination catalyst is prepared in situ. They are prepared from hydrofluorination catalyst precursors, such as $FeCl_3$, $SbCl_3$, $SbCl_5$, $MCl_5$, and M'Cl4F, and the like by charging the precursors with excess HF in situ in the reactor at effective temperatures. In an embodiment, the effective temperature for the preparation of the hydrofluorination catalyst ranges from about 70° C. to about 130° C., and in another embodiment, from about 83° C. to about 120° C., and in another embodiment, from about 85° C. to about 95° C. It is to be noted that although the temperature ranges for the preparation of the hydrofluorination catalyst in situ and the hydrofluorination reaction overlap, they do not need to be conducted at the same temperatures. However, in an embodiment, the preparation of the hydrofluorination catalyst in situ and the hydrofluorination reaction are conducted at the same temperatures.

The preparation of the hydrofluorination catalyst from a hydrofluorination catalyst precursor and the use thereof is illustrated hereinbelow with a representative example of the reaction of antimony chloride, e.g., antimony pentachloride, with HF, and the use thereof of the catalyst thus prepared in the hydrofluorination reaction described herein. But the procedure for making the latter hydrofluorination catalyst is applicable for preparing other hydrofluorination catalysts which are complexed with fluoride, such as $FeCl_{3-a}F_a$ (where a=0 to 3) from HF and $FeCl_3$; $SbCl_{3-b}F_b$ (where b=0 to 3) from HF and $SbCl_3$; $MCl_{5-c}F_c$ (where c=0 to 5 and M=Nb, Ta, or Mo); and $M'Cl_{4-d}F_d$ (where d=0 to 4, and M'=Sn, Ti or Zr) from HF and $M'Cl_4$, and the use thereof of these catalysts are demonstrated with the representative example of the hydrofluorination catalyst prepared from hydrogen fluoride and antimony halide, such as antimony pentachloride.

Active pentahalogenated antimony catalysts include compounds of the formula $SbCl_{5-x}F_x$ (where x=1, 2, 3, 4 or 5). $SbCl_3$ or $SbCl_5$ are typically employed as catalyst precursors, the starting source of the active halogenated antimony catalyst. $SbCl_5$ can be made to become an active pentahalogenated antimony catalyst by the addition of HF. For example, as a representative example, an antimony pentahalogenated hydrofluorination catalyst is prepared by reacting antimony chloride, such as antimony pentachloride, with excess HF in situ. In an embodiment, antimony pentachloride is charged with HF in excess prior to the addition of fluoroolefin to the reactor. Without limitation, $SbCl_3$ can be made to become an active pentahalogenated antimony species by the addition of $Cl_2$ which oxidizes it to $SbCl_5$ followed by fluorination by the addition of hydrogen fluoride (HF). $SbCl_3$ can also be made to become an active pentahalogenated antimony species by the addition of $F_2$ which oxidizes it to $SbCl_3F_2$. To convert $Sb^{+3}$ compounds such as $SbCl_3$ to $Sb^{+5}$ compounds such as $SbCl_{5-x}F_x$ (where x=1, 2, 3, 4, or 5), addition of $Cl_2$ followed by HF is preferred.

For example, in an embodiment, the antimony chloride, e.g., antimony pentachloride is charged with HF in an amount of the antimony chloride ranging from about 10 wt % to about 98 wt % and the HF ranging from about 90 wt % to about 2 wt %, wherein the sum of the total weight of the antimony chloride, such as antimony pentachloride, and HF, does not exceed 100 wt %. In another embodiment, the reactor is charged with a concentration of antimony halide, such as antimony chloride, e.g. antimony pentachloride at a concentration ranging from about 40 wt % to about 80 wt % and the concentration of the anhydrous liquid HF ranges from about 20 wt % to about 60 wt %; and in another embodiment, the reactor is charged with a concentration of antimony halide, such as antimony chloride, e.g. antimony pentachloride at a concentration ranging from about 50 wt % to about 70 wt % and the concentration of the anhydrous liquid HF ranges from about 30 wt % to about 50 wt %; and in another embodiment, the reactor is charged with a concentration of antimony halide, such as antimony chloride, e.g. antimony pentachloride at a concentration ranging from about 55 wt % to about 65 wt % and the concentration of the anhydrous liquid HF ranges from about 45 wt % to about 35 wt % and in a further embodiment, the reactor is charged with a concentration of antimony halide, such as antimony chloride, e.g. antimony pentachloride, at a concentration of about 60 wt % and the concentration of the anhydrous liquid HF is about 40 wt %.

An inactive trihalogenated antimony species may also be present as part of the reaction mixture; its presence may be due to reduction of the active pentahalogenated antimony species or it may be intentionally added. An inactive trihalogenated antimony species can be promoted to one of the aforementioned active pentahalogenated antimony catalyst species by oxidation with the addition of $Cl_2$ or $F_2$. Addition of $Cl_2$ is used in an embodiment of the present invention for promoting activity of an inactive trihalogenated antimony species because of its abundance and low cost, and because it is easier to handle. Reduction of the active pentahalogenated antimony catalyst species is the main cause of catalyst deactivation in the liquid phase fluorination reaction system. Thus, during the reaction or when charging the liquid HF with the antimony halide, additional catalyst or antimony species, such as, antimony pentachloride or antimony trichloride may be added to the reaction mixture. As used herein, the term "reaction mixture" denotes a mixture comprising HF, fluoroolefin and the hydrofluorination catalyst.

As used herein, unless indicated to the contrary, concentrations are in wt % or weight %. For example, when referring to the wt % of antimony halide, such as antimony chloride, in liquid HF, the "weight %" or "wt %" refers to the weight % of antimony halide, e.g., $SbCl_5$, present in the reactor with the remaining weight assumed to be HF and/or HF and an inactive halogenated antimony species (i.e., $SbCl_3$). For example, charging 20 kg of $SbCl_5$ and 80 kg of HF to a reactor represents a 20 wt % concentration, whereas charging 49 kg of $SbCl_5$, 41 kg of HF, and 10 Kg of $SbCl_3$ to a reactor represents a 49% wt concentration. Still another example is charging 50 kg of $SbCl_3$ precursor to the reaction; after enough $Cl_2$ is added to produce 25 kg of $SbCl_5$, 30 kg of $SbCl_3$ remains. 27 kg of HF is subsequently added to the reactor which represents a 30 wt % $SbCl_5$.

Incremental amounts of $SbCl_5$ may be added during catalyst runs to maintain the desired minimum 90% conversion and selectivity described herein. Alternatively, if $SbCl_3$ is intentionally added to HF and precursor catalyst or during the hydrofluorination reaction, an amount of $Cl_2$ and HF can be added to promote some of the $SbCl_3$ to active hydrofluorination catalyst in situ to maintain the desired minimum 90% conversion and selectivity.

In another embodiment, the 2-chloro-1,1,1,2-tetrafluoropropane being formed is at both a conversion of about 90% or more of the 2-chloro-3,3,3-trifluoropropene (HCFO-1233xf) initially present and a selectivity to 1,1,1,2,2-pentafluoropropane of about 10% or less by adding antimony pentachloride periodically in amounts ranging from about 0.5% to about 10% by weight of the total weight of antimony pentachloride and HF in the reactor. In an embodiment, the addition of hydrofluorination catalyst precursor, such as antimony pentachloride is periodic, as described herein, while in another embodiment, the addition of hydrofluorination catalyst precursor is continuous.

The HF in the reaction can be added either as a liquid or gas. If a liquid, it is added through an inlet into the reactor; and if it is a gas, it is bubbled into the reactor through an inlet through a gas injector, such as a sparger.

The fluoroolefin in the reaction can be either a liquid or solid or gas. If it is a solid, it may be added directly to the reactor. If a liquid, it is added through an inlet into the reactor; and if it is a gas, it is bubbled into the reactor through an inlet through a gas injector, such as a sparger.

The HF and fluoroolefin can be fed into the reactor through a single, common inlet, or separately through separate feed inlets.

To help maintain the reaction mass at the desired operating temperature, the HF and/or fluoroolefin can be vaporized and/or preheated to add supplemental heating in combination with or instead of heating provided through the reactor jacket using a heat transfer fluid, for example a heat transfer fluid such as steam fed to the jacket.

The reactor contains a reaction zone equipped with a stirrer. The charging of the hydrofluorination catalyst precursor and anhydrous liquid HF and the reaction mixture comprised of the fluoroolefin, hydrogen fluoride and the hydrofluorination catalyst are independently stirred at a sufficient rate so as to minimize or eliminate channeling. However, on the other hand, if the stirring is too rapid during the hydrofluorination reaction, there is an increased probability of overfluorination, thereby decreasing conversion and selectivity. Thus, the inventors have found a range for the speed of stirring in both the preparation of the hydrofluorination catalyst (if prepared in situ) and the hydrofluorination which avoids or minimizes channeling, on the one hand, and, on the other hand, avoids and minimizes overfluorination. In an embodiment, the stirrer is being rotated independently in the reaction of liquid HF and the hydrofluorination precursor, if the catalyst is prepared in situ and in the hydrofluorination reaction at a speed ranging from about 1 rpm to about 200 rpm. Thus, in an embodiment, the stirrer is rotated independently in these two processes at a speed of about 200 rpm or less, and in another embodiment, at a speed of about 175 rpm or less, and in another embodiment, at a speed of about 150 rpm or less, and in another embodiment, of about 125 rpm or less, and in still another embodiment, of about 100 rpm or less and in a further embodiment, of about 75 rpm or less and in still another embodiment, of about 50 rpm or less and in a further embodiment, in about 25 rpm or less. However, it is important that the reaction mass is mixed, so that the HF and catalyst precursor, if the catalyst is prepared in situ, and the fluoroolefin and the HF are stirred so as to minimize and/or avoid channeling. For example, the stirrer is rotated in the reaction of the HF and hydrofluorination catalyst precursor and in the reaction of HF and the fluoroolefin in the presence of the active fluorination catalyst independently at a speed of about 1 rpm or more, such as for example, of about 5 rpm or more, in an embodiment, while in another embodiment, of about 10 rpm or more, and in a still further embodiment of about 15 rpm or more, and in still further embodiment, of about 20 rpm or more, and in a further embodiment of about 25 rpm or more, and in a still further embodiment of about 30 rpm, and in still embodiment of about 35 rpm or more and in still embodiment, of about 40 rpm or more, and in a further embodiment of about 45 rpm or more. In an embodiment, the HF, fluoroolefin and active hydrofluorination catalyst reaction mixture, and the anhydrous liquid HF and hydrofluorination catalyst precursor, if the catalyst is prepared in situ, are independently stirred at a speed ranging from about 1 rpm to about 200 rpm, while in another embodiment, the stirring is effected at a rate of about 5 rpm to about 150 rpm, and in another embodiment, from about 10 rpm to about 125 rpm, while in another embodiment, from about 15 to about 100 rpm, and in another embodiment, from about 20 to about 75 rpm, while in another embodiment, from about 25 to about 50 rpm. Of course, the stirring for both processes independently can be effected at any speed ranging from about 1 to about 200 rpm, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 rpm. However, as a practical matter, if the catalyst precursor is prepared in situ, then the process for forming the catalyst and the process for the hydrofluorination reaction in an embodiment are stirred at the same rate, although this is not necessary.

The reactor is comprised of materials suitable for a fluorination reaction. The reactor zones are constructed from materials resistant to the corrosive effects of hydrogen fluoride (HF) and catalyst, e.g., metal or metal alloy lined with a fluoropolymer such as PFA or PTFE as known in the art.

FIG. 1 illustrates generally a cylindrical reactor 100 according to one exemplary embodiment of the reactor for the hydrofluorination reaction, according to an aspect of the present invention. The reactor contains the catalyst, which is either suspended or solubilized in the liquid present in the reactor, such as hydrofluoric acid. Sufficient catalyst is present to catalyze the hydrofluorination reaction.

In an embodiment the shape of the reactor will be cylindrical with the straight edge or axis of the cylinder running in the vertical direction. As used herein, the cylinder length as the "L" in L/D refers to the cylinder straight edge length parallel to the axis as measured in the vertical direction, and the cylinder diameter as the "D" in L/D refers to the cylinders width as measured in the radial direction. The reactor may optionally have in addition rounded or dished heads as part of the reactor design on either or both of the top or bottom of the cylinder reactor body that will further add to the overall height of the reactor.

The reactor 100 has a relatively large length/diameter (L/D) ratio. In an embodiment, it is about 2:1 or greater. In another embodiment, the L/D ratio is about 3:1 or greater. In still another embodiment, it is about 4:1 or greater. In still another embodiment, it is about 5:1 or greater, while still in another embodiment, it is about 6:1 or greater. In another embodiment, L/D is about 7:1 or greater. In a still further embodiment, L/D is about 8:1 or greater. In a still further embodiment, L/D is about 9:1 or greater. Further, in another embodiment, L/D is about 10:1 or greater. However, for practical purposes, the L/D ratio should be no larger than about 20:1. Thus, in an embodiment, the L/D ratio ranges from about 2:1 to about 20:1. In another embodiment, the L/D ratio ranges from about 3:1 to about 15:1. In still another embodiment, the L/D ratio ranges from about 4:1 to about 10:1.

The use of a large L/D ratio of, for example at least 2:1, or 3:1, or 4:1, or 5:1, or 6:1 or 7:1 or 8:1 or 9:1 or 10:1 or larger, allows for more residence time in the reactor for the same volume of reaction mixture (compared to a low L/D ratio) while providing easy reactor level control. In one embodiment the reactor vessel has an L/D ratio greater than or equal to typical existing fluorocarbon commercial scale reactors. One of the typical designs of such existing reactors has been disclosed in U.S. Pat. No. 7,102,040 assigned to Honeywell International, the disclosure of which is hereby incorporated herein by reference.

The reactor has at least one inlet 122 and at least one outlet 124, as shown schematically in FIG. 1. The inlet and outlet have valves which open and close. When the inlet valve is open, the feed, such as HF, fluoroolefin or $Cl_2$ can enter into the reactor; when closed, the feed cannot enter into the reactor. Similarly, the outlet has a valve, which when opened, permits the products formed from the hydrofluorination reaction and excess HF and side products to exit from the reactor. In an embodiment, the inlets and outlets are located in different areas of the reactor, that is, the at least one inlet 122 is on the bottom of the reactor and the at least one outlet 124 is on the top on the same side or opposite side of the reactor or the at least one inlet is on the top and the at least one outlet is on the bottom, on the same side or opposite side of the reactor. In one embodiment, the inlet comprises a dip tube, a gas injector or the like, such as a sparger, to bubble gaseous feed into the reactor. Although not shown in FIG. 1, in an embodiment, the reactor has an inlet for the fluoroolefin and a separate inlet for chlorine gas, which is used to regenerate spent catalyst.

Throughout this disclosure, a longitudinal direction is defined as a vertical direction extending from the top of the reactor to the bottom of the reactor, substantially parallel to the axis of the substantially cylindrical reactor; a radial direction is defined in a plane perpendicular to the longitudinal direction, extending from a center in the plane. The reactor 100 contains at least one stirrer 140 located radially at about the center of the reactor, which stirrer 140 contains a shaft 180 extending longitudinally upward from about the bottom of the reactor to approximately the top of the reactor. Typically, the bottom of the shaft 180 does not touch the bottom of the reactor; the shaft 180 is located at a distance sufficient from the bottom of the reactor so that it can rotate on its longitudinal axis without touching the bottom of the reactor. Alternately the shaft 180 may be mounted onto a bearing or any suitable supporting structure fitted into the bottom of the reactor 100 that will allow the shaft to rotate around its axis freely, but reduces its ability to move closer to the side walls of the reactor, in which case the potential oscillation of the bottom end of the shaft can be avoided.

The top of the shaft 180 extends outward from the reactor and is connected to a motor 160. However, a person of ordinary skill in the art understands that the top of the shaft 180 may be mounted onto any of several manners of seals and couplings that will help keep the reactor contents within the reactor yet permit the shaft to be rotated.

As shown in FIG. 1, the plurality of blades 142 is fixedly attached to the shaft 180, so that the rotation of the shaft 180 can be translated to the rotation of the blades 142. For example, the blades 142 can be fixedly inserted into slots or voids formed in the shaft 180 or formed integrally with the shaft 180. In another embodiment, the shaft 180 is attached to one or more groups of blades 142 which are disposed in an offset manner longitudinally along the shaft 180. As described above, the reactor design of this invention includes a multi-bladed stirrer, for example, an offset multi-bladed stirrer that will rotate at less than about 200 rpm, for the purpose of eliminating channeling. The wetted stirrer parts can be made of, or lined with fluoropolymer corrosion resistant materials.

As shown in FIG. 1, four groups of blades 142, from the top to the bottom of the reactor, can be provided. However, any number of groups of blades can be used provided they sufficiently stir the reactor contents to prevent channeling within the reaction vessel. For example, the first and third groups of blades can be the same and the second and the fourth groups of blades can be the same. The blades 142 may be any shape, although in an embodiment of the present invention, they are rectangular, trapezoidal, conical, oval or spherical. The blades may be pitched up or down to promote axial mixing. The blades may be any diameter, as long as they are at least sufficient distance from the wall of the reactor so that when the shaft rotates, they do not come into contact with the walls on the sides of the reactor or with each other. The length of the blades should be such that they are within a relatively short distance from the inside wall of the reaction vessel to prevent channeling close to the walls. In an embodiment agitator blade dimensions are where the diameter of blades (tip to tip) are between 25% and 90% of the internal diameter (D) of the reactor; with the blade height (vertical height) of the agitator blades ranging from 10 to 50% of the diameter of the blades (tip to tip).

In one embodiment, if the shaft 180 contains two groups of blades 142, they are oriented at about ⅓ and about ⅔ of the length of the shaft; if the shaft contains a plurality of blades 142, in an embodiment, the blades 142 extend from the bottom of the shaft to the area on the shaft that is about at the level of the liquid in the reactor. The blades 142 can be about equally spaced apart, or they can be not equally spaced apart. The spacing between the blades may depend on the distribution of the reactants within the reactor 100 and any other practical considerations. In this embodiment, the blades are sufficiently far apart so that when the reactor rotates, they do not impede the rotation of the shaft or each other. The blades 142 in one embodiment all have the same shape and are of the same size, although in other embodiments, they may have different shapes and be of different sizes. The blades 142 may be oriented at any angle ranging from 0° to about 90° with respect to a horizontal plane within which the same group of blades are disposed. In addition, rather than extending substantially perpendicular from the shaft 180, the blades 142 can form an angle ranging from 0° to about 90° with respect to the shaft 180. However, the blades may not be all oriented or angled in the same direction.

Figure 2:
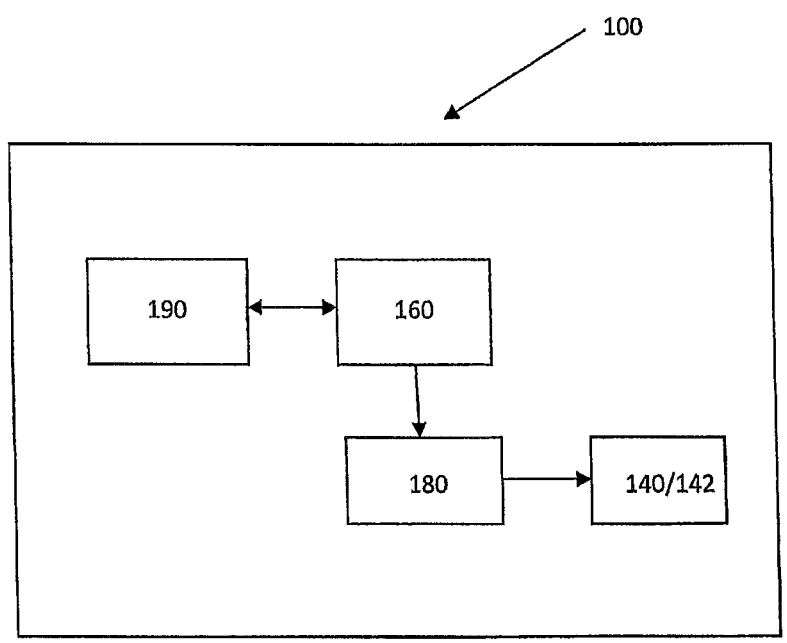
FIG. 2 is a block diagram of the reactor shown in FIG. 1, illustrating how the rotation of a stirrer of the reactor is controlled.

As shown in FIG. 2, the reactor 100 further includes a controller 190 in communication with the motor 160 for controlling the rotation speed of the shaft 180. The controller 190 can be any form of a computer, processor, circuit or the like, which can be programmed to maintain database and implement a predetermined algorithm. In this embodiment, the controller 190 is programmed or otherwise designed to control the rotational speed of the shaft.

In another embodiment, the reactor is also capable of being heated or cooled to keep the reaction temperature at a set, desired temperature, as well as at a desired pressure. In order to heat or cool the reactor, the reactor is equipped with a heating or cooling means which heats or cools the fluid in the reactor, using apparatus known to one of ordinary skill in the art. For example, in an embodiment, the reactor is equipped with a jacket (not shown). The jackets surround each reactor, partially or wholly. Sufficient amount of the reactor is jacketed so that it can heat or cool the fluid inside the reactor. In another embodiment, the HF and fluoroolefin feeds may be heated or cooled prior to being fed to the reactor, instead of or as a supplement to any heat provided by way of a reactor jacket.

The hydrofluorination reaction is conducted in a reactor described herein below under conditions effective to hydrofluorinate the fluoroolefin. In an embodiment, the reaction is conducted at a temperature ranging from about 70° C. to about 130° C., while in another embodiment, it is conducted at a temperature of about 83° C. to about 120° C., while in still another embodiment, it is conducted at a temperature of about 85° C. to about 95° C.

In accordance with the present invention, the reactor contains the catalyst. Hydrofluoric acid is added to the reactor through the feed inlet. The fluoroolefin also enters the reactor through a feed inlet. The hydrofluorination is carried out under conditions effective to provide a conversion of at least about 90%, in one embodiment, while in another embodiment of at least about 93% and in still another embodiment of at least about 96%. The reactor is preheated to the desired fluorination reaction temperature while or before the HF is added to the reactor. Additional vaporized HF may be added, if desired. The fluoroolefin, especially vaporized fluoroolefin, is fed into the reactor through the inlet. The fluoroalkane formed exits from the reactor through the outlet. In an embodiment, the fluoroalkane formed is a gas, and thus, once formed, it exits the reactor as a gas, where it may be collected and condensed, if necessary and purified by techniques known in the art, such as by distillation, after the gas has been condensed.

The reaction described herein may be conducted in a liquid-phase reactor operating in batch, semi-batch, semi-continuous, or continuous modes. The reaction described herein may be conducted in a liquid-phase reactor operating in batch, semi-batch, semi-continuous, or continuous modes. The reaction can be run batch wise with the inlet and outlet valves closed while the reaction is taking place. Alternatively, the reaction can be conducted continuously with the inlet and outlet valves continuously open and HF and fluoroolefin being added continuously to the reactor and products (fluoroalkane and side products) being removed or exiting in the gaseous state continuously from the reactor through the outlet valve. In another embodiment, the reaction is conducted semi-continuously.

The reactor pressure in the liquid-phase process is not critical and in batch reactions is usually the autogenous pressure of the system at the reaction temperature. In a continuous process it is possible to set the pressure of the reactor in such a way that the lower boiling products of the reaction are vented from the reactor, optionally through a packed column or condenser.

The conversion and selectivity must be sufficiently high in the reaction per catalytic run to be useful commercially. Since these are commercial processes, it is imperative that the conversion of the fluoroolefin staring material and the selectivity to the desired fluoroalkane each be at least higher than 90% for at least about 500 hours and in another embodiment, at least about 1000 hours, and in still a further embodiment at least about 2,000 hours per catalytic run without the necessity of replacing the catalyst.

The catalysts can be readily regenerated by any means known in the art if they become deactivated. One suitable method of regenerating the catalyst involves flowing a stream of chlorine through the inlet into the reactor containing the catalyst. For example, from about 0.001 to about 0.2 lb per hour (0.45 to 90 grams per hour) of chlorine can be added to the liquid phase reaction for every pound of fluorination catalyst. This may be done, for example, for about 1 to about 2 hours or continuously at a temperature of from about 50° C. to about 130° C.

The inventors have found that in conducting the hydrofluorination reaction of fluoroolefin in a liquid, in the absence of agitation, the conversion to the fluorocarbon initially was high, but the conversion to the fluorocarbon dropped dramatically to an unacceptable level after a short period of time.

Moreover, the inventors have found that channeling affects the conversion to the fluoroolefin. By channeling, it is meant that the reaction mixture contains dead space whereby some of the molecules of the fluoroolefin and/or catalyst do not come into contact with one another and HF and thus cannot react. This was surprising since the reaction is conducted under heat and so it was thought that the heat would cause sufficient agitation of the liquid so that the molecules of fluoroolefin and HF can come into contact with the catalyst. In a successful reaction, the conversion to the fluorocarbon is to be greater than about 90%.

Various solutions were contemplated. One solution to this problem was to increase the concentration of the catalyst. The inventors have found that when the concentration of the catalyst was increased, again initially the conversion to the fluorocarbon was satisfactory, but after a short period of time, it became unsatisfactory, dropping to an unacceptable level.

The inventors have found that the reaction mixture needed to be stirred. However, if the stirring of the liquid were insufficient then the conversion rate to the fluoroalkane from the fluoroolefin was not maintained at a satisfactory level for a sufficient amount of time. On the other hand, if the stirring were too high, the inventors have found that the % conversion and/or % selectivity were too low as overfluorination occurs. The inventors have found that the channeling effect is avoided and/or minimized when the rotation speed of the shaft 180 is about 200 revolutions per minute or less; in another embodiment, the rotation speed of the shaft 180 is about 100 rpm or less and in still further embodiment, the rotation speed of the shaft 180 is about 50 rpm or less. However, the shaft 180 needs to rotate at a minimum rate of about 5 rpm and at a maximum rate of 200 rpm. At this rate, the inventors have found that such speed provides sufficient mixing for the reactants, 1233xf and HF to interact with the catalyst and effect the hydrofluorination reaction.

When the reaction is conducted in the reactor as described hereinabove, the inventors have found an effective way to hydrofluorinate the fluoroolefin to produce the fluoroalkane with high conversion and high selectivity for a satisfactory amount of time, for example at least about 500 hours per catalytic run before regenerating or replacing catalyst.

As used herein, the term "catalytic run" refers to the amount of time that the hydrofluorination reaction produces the fluoroalkane with greater than about 90% conversion of the fluoroolefin and a selectivity of greater than about 90% of the fluoroalkane. In an embodiment of the present invention, the catalyst is regenerated when the fluoroolefin conversion is less than about 90% conversion. Typically, for a commercial process, the hydrofluorination reaction is run over 500 hours, and in another embodiment more preferably over 1000, and still in another embodiment preferably over about 2000 hours before the conversion rate falls below 90%.

The inventors have found that mechanical stirring combined with high catalyst concentration makes a big difference in the length of time that the catalyst was overactive. In the low L/D ratio stirred laboratory reactor a high catalyst concentration is needed to provide stable reactor operation, but this is at the expense of excessive 245cb formation. It appears that the problem of excessive 245cb formation in the Step (2) reaction is predominantly due to catalyst over-activity, which can be solved by using a diluted catalyst, provided there is sufficient residence time that is inherent in a high L/D ratio reactor design.

(1) The high L/D reactor combined with stirring provides a longer residence time per equal catalyst reaction mixture volume;
(2) The high L/D reactor combined with stirring facilitates the input of heat;
(3) The high L/D reactor combined with stirring facilitates the control of the reactor level.

As described above, instead of a typical commercial mechanical agitator, the reactor design of this invention includes a multi-bladed stirrer, preferably an offset multi-bladed stirrer that will rotate at less than about 200 rpm, for the purpose of eliminating channeling. The wetted stirrer parts can be made of, or lined with fluoropolymer corrosion resistant materials. The length of the blades should be such that they are within a relatively short distance from the inside wall of the reaction vessel to prevent channeling close to the walls. The present inventors have found that these problems can be mitigated by the use of a slow agitation speed, i.e., agitation at about 200 rpm or less, and in another embodiment, 100 rpm or less and in still another embodiment, about 50 rpm or less.

The process of the invention may be employed, for example, as part of a larger process to make compounds such as 2,3,3,3-tetrafluoropropene (1234yf). For example, the process of the invention can be the second step of the three-step process to make 1234yf as described above. In a preferred embodiment in this regard, the present invention comprises a step of an integrated manufacturing process for making 2,3,3,3-tetrafluoropropene. The preferred starting material for this process is one or more chlorinated compounds according to Formulae I, II and/or III:

$$CX_2=CCl—CH_2X \qquad \text{(Formula I)}$$

$$CX_3—CCl=CH_2 \qquad \text{(Formula II)}$$

$$CX_3—CHCl—CH_2X \qquad \text{(Formula III)}$$

wherein X is independently selected from F, Cl, Br, and I, provided that at least one X is not fluorine. Preferably, these compounds contain at least one chlorine, more preferably a majority of X is chlorine, and even more preferably all X is chlorine. Preferably, the method generally comprises at least three reaction steps:

Step 1:
In the first step, a starting composition including one or more compounds having Formula (I), (II) or (III), preferably 1,1,2,3-tetrachloropropene (TCP) and/or 2,3,3,3-tertachloropene, and/or 1,1,1,2,3-pentachloropropane (240db), reacts with anhydrous HF in a first vapor phase reactor (fluorination reactor) to produce a mixture of 2-chloro-3,3,3-trifluoropropene (1233xf) and HCl. Preferably the reaction occurs in the presence of a catalyst, such as a fluorinated chromium oxide. The reaction is conducted in a first vapor phase reactor, preferably at a reaction temperature of about 200-400° C. and a reaction pressure of about 0-200 psig. The effluent stream exiting the vapor phase reactor may optionally comprise additional components, such as un-reacted HF, heavy intermediates, and HFC-245cb.

In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

In an embodiment, the 1233xf produced in Step 1 is condensed to collect the liquid and then distilled to separate the 1233xf from the impurities and the product purified 1233xf collected for use in step 2.

Step 2:
In the second step, the process of the present invention as described herein is employed whereby 1233xf, produced in Step 1, is fed through the inlet into the reactor, and subjected to hydrofluorination as described herein. Since the Step (2) reaction does not produce any HCl co-product, the mixing in the commercial scale reactor (and in the lab-re: channeling in the 'bubble column' reactor) in all likelihood, will be insufficient, which will then require the reactor design to have some method of agitation, as described herein. In an embodiment, the 1233xf is converted at more than about 95% to 244bb, with any 245cb by-product being generated at less than about 2% by weight. In an embodiment, prior to step 3, the 245cb by-product is separated from the 244bb by techniques known in the art.

Step 3:

In the third step, the 244bb, produced from Step 2 in accordance with the invention, is fed to a second vapor phase reactor (dehydrochlorination reactor) to be dehydrochlorinated to make the desired product 2,3,3,3-tetrafluoropropene (1234yf). This reactor contains a catalyst that can catalytically dehydrochlorinate 244bb to make 1234yf.

The catalysts here may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono- and bi-valent metal halides and their mixtures/combinations. Component metals include, but are not limited to $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Examples of catalysts include activated carbon, stainless steel (e.g. SS 316), austenitic nickel-based alloys (e.g. Inconel 625), nickel, fluorinated 10% CsCl/MgO, and 10% CsCl/$MgF_2$. The reaction temperature is preferably about 300-550° C. and the reaction pressure is preferably about 0-150 psig. Preferably, the reactor effluent is fed to a caustic scrubber or to a distillation column to remove the by-product of HCl to produce an acid-free organic product which, optionally, may undergo further purification.

The following non limiting examples further illustrate the invention.

Example 1

600 kg of $SbCl_5$ and 9070 kg of HF, a 15:85 wt. ratio of $SbCl_5$ and HF, are charged to a slowly stirred bubble column reactor (L/D of 6:1) as shown in FIG. 1, wherein the length of the reactor is about 830 cm and the diameter of the reactor is about 140 cm. The reactor has 4 groups of 4 paddle blades that are rectangular in shape. The diameter of the blades is 126 cm (from blade tip to opposing blade tip) and the height of the blades is 30 cm. The groups of blades are attached to the shaft equal distances apart with the lowest group of blades at about 30 cm from the bottom of the reactor. The shaft of the stirrer is stabilized to prevent wobbling by being inserted in a bearing cup at the bottom of the reactor. The mixture is heated to 90° C. with the stirrer turned on at a speed of 50 RPM. A pressure of 105 psig is maintained in the reactor by opening or closing a valve in the vapor space off gas line as needed. Gaseous HCFO-1233xf and gaseous HF are then continually fed directly into the reaction mixture through a sparger that is attached to the bottom of the reactor. The HCFO-1233xf is fed at a rate of 1202 kg/hr and HF is fed at a rate of 476 kg/hr. After an initial 50 hour catalyst conditioning stage, a reactor effluent stream consisting mainly of some unreacted HF and an organic composition of about 96 mole % of HFC-244bb, 3 mole % unreacted HCFO-1233xf, and 1 mole % 245cb exit the reactor for further processing for 750 hours before catalyst regeneration is required. $Cl_2$, which is fed through a separate nozzle with sparger connected to the bottom of the reactor, is then used to regenerate spent catalyst.

Example 2

A laboratory reactor using the slowly stirred bubble column design was built. The reactor consisted of a steam jacketed nominal 3.5" diameter×35" long PTFE lined pipe. The reactor was equipped with a variable speed magnetic drive powered stirrer. The stirrer consisted of a long PTFE coated shaft that was inserted into a bearing at the bottom of the reactor to prevent it from wobbling. Attached to the shaft were 3 PTFE stirrer devices. The first stirrer device was about 1" from the bottom of the reactor. The next was about 10" above the first and the third was about 10" above the second. Each of the three stirrer devices had 4 blades and the diameter of each stirrer device was 2.5" from blade tip to blade tip. Each blade on each of the three stirrer devices was a rectangular shape, with a ⅝" vertical height, angled at 45 degrees in relation to the agitator shaft such that they provide some amount of downflow axial catalyst mass fluid movement during operation. The stirrer devices were attached so the blades of each device were off-set from those of the other 2 devices to further prevent channeling.

675 grams of $SbCl_5$ and 5.5 lbs of HF were added to the reactor. This amounted to about a 20/80 wt % mixture of $SbCl_5$ to HF. The stirrer speed was brought to 18 rpm. The reaction contents were brought to and maintained at a temperature range of 85-89° C. The reactor pressure was brought to and maintained going forward at about 100 psig by opening or closing the valve in the product take-off line as needed. HFO-1233xf and HF feed rates of about 0.9 and 0.4 lb/hr respectively were then set (a mole ratio of HF to 1233xf of about 2.8:1).

The reaction was run for over 2300 hours at these conditions. The catalyst was "sweetened" with the addition of small increments of fresh catalyst or regenerated with $Cl_2$ several times during the run to keep high catalyst activity as can be appreciated by someone in the art who has knowledge of using $SbCl_5$ catalyst for liquid phase fluorination reactions. Excluding the first 50 hours of the run, the average 1233xf conversion for the run was 95.3 mole %. The average selectivity of 245cb for the run was 1.2 mole %. The average selectivity of the target product HCFC-244bb for the run was 98.7 mole %.

Example 3

The same slowly stirred bubble column designed reactor that was used in Example 2 was used for Example 3. The reactor consisted of a steam jacketed nominal 3.5" diameter x 35" long PTFE lined pipe. The reactor was equipped with a variable speed magnetic drive powered stirrer. The stirrer consisted of a long PTFE coated shaft that was inserted into a bearing at the bottom of the reactor to prevent it from wobbling. Attached to the shaft were 3 PTFE stirrer devices. The first stirrer device was about 1 inch from the bottom of the reactor. The next was about 10" above the first and the third was about 10 inches above the second. Each of the three stirrer devices had 4 blades and the diameter of each stirrer device was 2.5" from blade tip to blade tip. Each blade on each of the three stirrer devices was a rectangular shape, with a ⅝"

vertical height, angled at 45 degrees in relation to the agitator shaft such that they provide some amount of downflow axial catalyst mass fluid movement during operation. The stirrer devices were attached so the blades of each device were off-set from those of the other 2 devices to further prevent channeling.

3500 grams of $SbCl_5$ and 4.5 lbs of HF were added to the reactor. This amounted to about a 63/37 wt % mixture of $SbCl_5$ to HF. The stirrer speed was brought to 18 rpm. The reaction contents were brought to and maintained at a temperature range of 85-89° C. The reactor pressure was brought to and maintained going forward at about 100 psig by opening or closing the valve in the product take-off line as needed. HFO-1233xf and HF feed rates of about 0.98 and 0.37 lb/hr respectively were then set (a mole ratio of HF to 1233xf of about 2.5:1).

The reaction was run for over 2500 hours at these conditions. After about the first 900 hours the catalyst was regenerated with $Cl_2$ several times during the run to keep high catalyst activity as can be appreciated by someone in the art who has knowledge of using $SbCl_5$ catalyst for liquid phase fluorination reactions. Excluding the first 100 hours of the run, the average 1233xf conversion for the run was 96.4 mole %. The average selectivity of 245cb for the run was 1.35 mole %. The average selectivity of the target product HCFC-244bb for the run was 98.60 mole %.

Comparative Example 1

A continuous Step (2) reaction using a tall, skinny, non-agitated reactor, described by some as a 'bubble column' reactor was performed. The length to diameter ratio (L/D ratio) of the reactor was about 14:1 (35 inches in length vs. 2.5 inches diameter).

About 650 grams of $SbCl_5$ and about 7 lbs of HF were initially charged to the reactor resulting in a 20 wt. % mixture of catalyst in HF. The reaction mass was brought to and maintained at ~90° C. and the reactor brought to and maintained going forward at around 100 psig pressure by opening or closing the valve in the top vapor take-off valve as needed. Continuous feeds of gaseous 1233xf and gaseous HF were then fed continuously to the reactor and it was found to be relatively easy to maintain a steady weight of reaction mixture in the reactor. HCFO-1233xf was fed at a rate of about 1.02 lb/hr and HF was fed at a rate of about 0.65 lb/hr. The amount of 245cb formation decreased to less than about 2% after about 45 hours of continuous on-stream time. However, in this Comparative Example, it was difficult to keep the conversion of 1233xf high for an extended period of time. Initially, the 1233xf conversion was about 96% but then decreased to less than about 90% after 150 hours of continuous on-stream time.

The failure to achieve consistently high conversion of 1233xf in the bubble column reactor was probably caused by channeling, and thus by insufficient mixing of the reaction mixture inside the reaction vessel. It is believed this channeling effect severely reduced the amount of catalyst that the 1233xf could come into contact with, thereby explaining the low conversion.

Comparative Example 2

Comparative Example 1 was repeated, but with a higher initial catalyst concentration, i.e., greater than about 60 wt. %, with the balance HF. It was otherwise run at the same operating conditions as Comparative Example 1. It was similarly found to be relatively easy to maintain a steady weight of reaction mixture in the reactor. The undesirable by-product 245cb formation was initially about 60% while the 1233xf conversion was greater than about 95%. The 245cb formation decreased to less than about 2% after about 60 hours of continuous reaction run time and decreased even further throughout the remainder of the run. The conversion of 1233xf remained consistent (between 95 mole % and 96 mole %) for about 280 hours of continuous run time, but it then decreased surprisingly quickly to about 82% over a 24 hour period. Again the loss of conversion can be attributed to "channeling" within the reaction mixture.

Comparative Example 3

This example was conducted using a jacketed PTFE lined vessel with an L/D ratio of about 1.3:1 and a PTFE agitator that could be operated up to a speed of 500 rpm. About 1 kg of $SbCl_5$ and about 3.6 kg of HF were initially charged to the reactor, which resulted in a reaction mixture slightly more concentrated in antimony catalyst (22 wt. % v. 20 wt. %) than what had been used in the bubble column reactor experiments of Comparative Examples 1 and 2 described above. For this experiment the agitator was operated at about 225 rpm. Maintaining a stable reaction mixture weight regardless of the 1233xf and HF feed rate was found to be difficult at best. The reaction mixture weight was found to be very sensitive to the amount of heat provided via steam flow to the reactor jacket and there was too much of a lag time between when steam flow was increased or decreased and changes in the reaction mixture weight to allow for stable control. It was felt that the high agitation rates in turn caused rapid changes in each of the reaction rate and product mix and in the effectiveness of the heat input to the reactor to the extent, such that the reaction mixture boil up rates changed too quickly to allow for adequate reactor weight and inventory control.

Comparative Example 4

In this example, the reactor had a low L/D of 1.3:1 and involved the addition of relatively large amounts (4 kg) of fresh charge of $SbCl_5$ catalyst and excess HF (6 lbs) for a catalyst concentration of about 60 wt. %. There was no 1233xf present at the beginning of the run. Only HF and $SbCl_5$ were charged to the reactor initially. In addition, the mixing speed was reduced to about 100 RPM for improved reactor operating control.

As expected, the 245cb selectivity was initially very high (76%, molar basis), but unlike the 'bubble column' reactor in Comparative Examples 1-2, the level of the undesirable 245cb remained relatively high (still about 2.5%, molar basis) throughout a 525 hr run. As described above, in Comparative Example 2, the 245cb selectivity using a high catalyst concentration was initially high (e.g., up to 60 mole %), but decreased to less than 2% after about 50 to 60 hours of reaction run time. The conversion of 1233xf remained consistent throughout (from 95 mole % to 96 mole %).

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

What is claimed is:

1. A hydrofluorination process which comprises reacting a fluoroolefin with anhydrous liquid HF to form a fluoroalkane in the liquid phase in the presence of a hydrofluorination catalyst in the reaction zone of a reactor, said reactor comprised of a reactor body having a length to diameter ratio of about 2:1 or greater; a stirred reaction zone containing said hydrofluorination catalyst, at least one inlet for supplying said HF and fluoroolefin to the reaction zone and at least one outlet for recovering said fluoroalkane, a stirrer disposed in the reaction zone and comprising a plurality of blades fixedly attached to a shaft drivable by a motor, said blades extending from about the bottom of the reaction zone to about the top of the reaction zone and said shaft extending on a longitudinal axis from the bottom of the reactor to the top of the reactor, said stirrer being rotated at a speed sufficient to form said hydrofluorination catalyst, to minimize channeling and to promote a swirling of the liquid to permit said mixing of the catalyst and fluoroolefin with the HF to effect the occurrence of hydrofluorination reaction with conversion of about 90% or greater and a selectivity of about 90% greater per catalytic run and avoid overfluorination, said stirrer being spun at a rotational speed ranging from about 1 rpm to about 200 rpm.

2. The process according to claim 1 wherein the hydrofluorination catalyst is prepared in situ in the reaction zone of the reactor from a hydrofluorination catalyst precursor.

3. The process according to claim 2 wherein the hydrofluorination catalyst precursor and anhydrous liquid HF are charged into the reaction zone in a concentration of said hydrofluorination catalyst precursor ranging from about 10 wt % to about 98 wt % and a concentration of the anhydrous liquid HF ranging from about 90 wt % to about 2 wt % at a temperature ranging from about 70° C. to about 130° C., said wt % of the total weight of anhydrous liquid HF and the hydrofluorination catalyst precursor not exceeding 100 wt % and stirring said hydrofluorination catalyst precursor and said anhydrous liquid HF at a speed ranging from about 1 rpm to about 200 rpm.

4. The process according to claim 3 wherein the hydrofluorination catalyst precursor and the anhydrous liquid HF are charged into the reaction zone at a concentration of said hydrofluorination catalyst precursor ranging from about 40 wt % to about 80 wt % and a concentration of the anhydrous liquid HF ranging from about 20 wt % to about 60 wt %.

5. The process according to claim 1 wherein the length to diameter ratio of the reactor is about 4:1 or greater.

6. The process according to claim 5 wherein the length to diameter ratio of the reactor is about 6:1 or greater.

7. The process according to claim 5 wherein the length to diameter ratio of the reactor is about 10:1 or greater.

8. The process according to claim 1 wherein the rotational speed of the stirrer ranges from about 10 to about 125 rpm.

9. The process according to claim 1 wherein the rotational speed of the stirrer ranges from about 20 rpm to about 75 rpm.

10. The process according to claim 1 wherein the rotational speed of the stirrer ranges from about 25 rpm to about 50 rpm.

11. The process according to claim 1 wherein the hydrofluorination reaction is conducted at a temperature ranging from about 70° C. to about 130° C.

12. A hydrofluorination process which comprises: (a) charging anhydrous liquid HF and a hydrofluorination catalyst precursor comprised of antimony pentahalide in the reaction zone of a reactor in a concentration of said hydrofluorination catalyst precursor ranging from about 10 wt % to about 98 wt % and a concentration of the anhydrous liquid HF ranging from about 90 wt % to about 2 wt % at a temperature ranging from about 70° C. to about 130° C., said wt % of the total of anhydrous liquid HF and hydrofluorination catalyst precursor not exceeding 100 wt % to form a hydrofluorination catalyst and (b) then reacting a fluoroolefin with anhydrous liquid HF to form a fluoroalkane in the liquid phase in the presence of said hydrofluorination catalyst prepared in step (a) in the reaction zone of a reactor at a temperature ranging from about 70° C. to about 130° C., said reactor comprised of a reactor body having a length to diameter ratio of about 2:1 or greater; a stirred reaction zone containing said hydrofluorination catalyst, at least one inlet for supplying said hydrogen fluoride in the liquid state and fluoroolefin to the reaction zone and at least one outlet for recovering said fluoroalkane, a stirrer disposed in the reaction zone and comprising a plurality of blades fixedly attached to a shaft drivable by a motor, said blades extending from about the bottom of the reaction zone to about the top of the reaction zone and said shaft extending on a longitudinal axis from the bottom of the reactor to the top of the reactor, said stirrer being rotated at a rotational speed sufficient to form the hydrofluorination catalyst, to minimize channeling and to promote a swirling of the liquid to permit said mixing of the catalyst and fluoroolefin with the hydrogen fluoride to effect the occurrence of hydrofluorination reaction with conversion of about 90% or greater and a selectivity of about 90% greater per catalytic run and avoid overfluorination, said stirrer being spun at a speed ranging from about 1 rpm to about 200 rpm.

13. The process according to claim 12 wherein the hydrofluorination catalyst precursor and the anhydrous liquid HF are charged into the reaction zone at a concentration ranging from about 40 wt % to about 80 wt % of said hydrofluorination catalyst precursor and a concentration of the anhydrous liquid HF ranging from about 20 wt % to about 60 wt %.

14. The process according to claim 12 wherein the length to diameter ratio of the reactor is about 4:1 or greater.

15. The process according to claim 14 wherein the length to diameter ratio of the reactor is about 6:1 or greater.

16. The process according to claim 14 wherein the length to diameter ratio of the reactor is about 10:1 or greater.

17. The process according to claim 12 wherein the rotational speed of the stirrer in step (a) and in step (b) independently range from about 10 to about 125 rpm.

18. The process according to claim 12 wherein the rotational speed of the stirrer in step (a) and in step (b) independently range from about 20 to about 75 rpm.

19. The process according to claim 12 wherein the rotational speed of the stirrer in step (a) and in step (b) independently range from about 25 to about 50 rpm.

20. The process according to claim 1 wherein the fluoroolefin is 2-chloro-3,3,3-trifluoropropene (1233xf) and the fluoroalkane is 2-chloro-1,1,1,2-tetrafluoropropane (244bb).

21. The process according to claim 1 wherein the reactor additionally comprises a controller in communication with the motor, wherein the controller is configured to rotate the stirrer at a speed sufficient to promote a swirling of the liquid to permit said mixing of the catalyst and fluoroolefin with the hydrogen fluoride to effect the occurrence of hydrofluorination reaction and be maintained with greater than about 90% conversion and greater than about 90% selectivity per catalytic run and to minimize channeling.

22. The process according to claim 12 wherein the reactor additionally comprises a controller in communication with the motor, wherein the controller is configured to rotate the stirrer at a speed sufficient to promote a swirling of the liquid to permit said mixing of the catalyst and fluoroolefin with the hydrogen fluoride to effect the occurrence of hydrofluorination reaction and be maintained with greater than about 90% conversion and greater than about 90% selectivity per catalytic run and to minimize channeling.

23. A process to prepare 2,3,3,3-tetrafluoropropene (1234yf) comprising:
   a) providing a starting composition comprising at least one compound having a structure selected from Formula I, II and II:

$$CX_2=CCl-CH_2X \quad \text{(Formula I)}$$

$$CX_3-CCl=CH2 \quad \text{(Formula II)}$$

$$CX_3-CHCl-CH_2X \quad \text{(Formula III)}$$

wherein X is independently selected from F, Cl, Br and I, provided that at least one of X is not F;
   b) contacting said starting composition with HF under conditions effective to produce a first intermediate composition comprising 2-chloro-3,3,3-trifluoropropene (1233xf);
   c) hydrofluorinating said first intermediate composition comprising 1233xf with HF in the presence of a hydrofluorination catalyst in accordance with the process of claim 1 or 18 to produce 2-chloro-1,1,1,2-tetrafluoropropane (244bb) and
   d) dehydrochlorinating at least a portion of said 244bb to produce a reaction product comprising 1234yf.

* * * * *